(12) United States Patent
Bennett, Jr.

(10) Patent No.: US 7,157,480 B2
(45) Date of Patent: Jan. 2, 2007

(54) USE OF PRAMIPEXOLE TO TREAT AMYOTROPHIC LATERAL SCLEROSIS

(75) Inventor: James P. Bennett, Jr., Crozet, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 10/496,714

(22) PCT Filed: Dec. 2, 2002

(86) PCT No.: PCT/US02/39970

§ 371 (c)(1),
(2), (4) Date: May 26, 2004

(87) PCT Pub. No.: WO03/049705

PCT Pub. Date: Jun. 19, 2003

(65) Prior Publication Data

US 2005/0032856 A1 Feb. 10, 2005

Related U.S. Application Data

(60) Provisional application No. 60/339,383, filed on Dec. 11, 2001, provisional application No. 60/347,371, filed on Jan. 11, 2002.

(51) Int. Cl.
*A61K 31/425* (2006.01)
(52) U.S. Cl. .................................................. 514/367
(58) Field of Classification Search ................ 514/367
See application file for complete search history.

(56) References Cited

U.S. PATENT DOCUMENTS 4,731,374 A 3/1988 Griss et al.
5,650,420 A * 7/1997 Hall et al. ................... 514/367
6,156,777 A 12/2000 Hall et al.
6,187,802 B1 2/2001 Cheetham et al.

FOREIGN PATENT DOCUMENTS

| WO | WO 0113902 A2 | 3/2001 |
| WO | WO 0122820 A1 | 4/2001 |
| WO | WO 0162249 A1 | 8/2001 |

OTHER PUBLICATIONS

Cassarino et al., An evaluation of the role of mitochondria in neurodegenerative diseases: mitochondrial mutations and oxidative pathology, protective nuclear responses and cell death in neurodegeneration., Brain Research Reviews, 29m 1999, pp. 1-25.*
Hardy et al. Genetic Classification of Primary Neurodegenerative Disease, Science: Nov. 6, 1998, vol. 282 No. 5391, pp. 1075-7079.*
Roberecht, Wim (2000). "Oxidative stress in amyotrophic lateral sclerosis." J. Neurol, vol. 247, pp. 1/1-1/6.
Cassarino, David S. and Bennett, Jr., James P. (1999). "An evaluation of the role of mitochondria in neurodegenerative diseases: mitochondrial mutations and oxidative pathology, protective nuclear responses, and cell death in neurodegeneration." Brain Research Reviews, vol. 29, pp. 1-25.
Swerdlow, R.H., Parks, J.K., Cassarino, D.S. Trimmer, P.A., Miller, S.W., Maguire, D.J., Sheehan, J.P., Maguire, R.S. Pattee, G., Juel, V.C. Phillips, L.H., Tuttle, J.B., Bennett, Jr., J.P., Davis, R.E. Parker, Jr., W.D. (1998). "Mitochondria in Sporadic Amyotrophic Lateral Sclerosis." Experimental Neurology, vol. 153, pp. 135-142.

* cited by examiner

*Primary Examiner*—Ardin H. Marschel
*Assistant Examiner*—Donna Jagoe
(74) *Attorney, Agent, or Firm*—Pabst Patent Group LLP

(57) ABSTRACT

The present invention is directed to compositions comprising pramipexole and the use of such compositions to treat neurodegenerative diseases such as amyotrophic lateral sclerosis (ALS). As shown in FIG. 6B the mean +/− SEM serum 2,3-DHBA levels for the 12 ALS participants decreased significantly after pramipexole treatment.

10 Claims, 8 Drawing Sheets hrs after 1.3 gm ASA

USE OF PRAMIPEXOLE TO TREAT AMYOTROPHIC LATERAL SCLEROSIS

RELATED APPLICATIONS

This application claims priority under 35 U.S.C. §119(e) to provisional patent application No. 60/339,383 filed Dec. 11, 2001 and Ser. No. 60/347,371 filed Jan. 11, 2002, the disclosures of which are incorporated herein.

U.S. Government Rights

This invention was made with United States Government support under Grant Nos. NS35325, AG14373, NS39788 and NS39005 awarded by National Institutes of Health. The United States Government has certain rights in the invention.

FIELD OF THE INVENTION

The present invention relates to the use of pramipexole (2-amino-4,5,6,7-tetrahydro-6-propylaminobenzathiazole) to treat neurodegenerative diseases. More particularly the invention is directed to the use of the substantially pure sterioisomer R(+) 2-amino-4,5,6,7-tetrahydro-6-propylaminobenzathiazole and the pharmacologically acceptable salts thereof as a neuroprotective agent to treat neurodegenerative diseases.

BACKGROUND OF THE INVENTION

Neurodegenerative diseases (NDD) such as Alzheimer's disease (AD) and Parkinson's disease (PD) arise from the accelerated loss of certain populations of neurons in the brain. Parkinson's (PD) and Alzheimer's (AD) diseases usually appear sporadically without any obvious Mendelian inheritance patterns, but may show maternal biases. Although rare or uncommon inherited forms of adult NDD exist, the relevance of pathogenesis in these autosomal genetic variants to the much more commonly occurring sporadic forms is a subject of intense debate.

Accumulating evidence provides compelling support that a primary etiologic component of sporadic adult NDD relates to mitochondrial dysfunction and the resulting increased cellular oxidative stress. PD and AD brains and non-CNS tissues show reductions in mitochondrial electron transport chain (ETC) activity. When selectively amplified in cytoplasmic hybrid ("cybrid") cell models, mitochondrial genes from PD (Swerdlow, et al, Exp Neurol 153:135–42, 1998) and AD (Swerdlow, et al, Exp Neurol 153:135–42, 1997) subjects recapitulate the ETC deficits, produce increased oxidative stress and a variety of other important mitochondrial and cellular dysfunctions. The combined weight of evidence from tissue studies and cybrid models of sporadic PD and AD suggests that relief of oxidative stress, by agents capable of scavenging oxygen free radicals and protecting cells from mitochondrially generated cell death, be considered as a primary characteristic of compounds developed as neuroprotective agents for these diseases (Beal, Exp Neurol 153:135–42, 2000).

Oxidative stress has also been associated with the fatal neurodegenerative disorder amyotrophic lateral sclerosis (ALS). ALS, also known as Lou Gehrig's disease, is a progressive, fatal neurodegenerative disorder involving the motor neurons of the cortex, brain stem, and spinal cord. It is a degenerative disease of upper and lower motor neurons that produces progressive weakness of voluntary muscles, with eventual death. The onset of disease is usually in the fourth or fifth decade of life, and affected individuals succumb within 2 to 5 years of disease onset. ALS occurs in both sporadic and familial forms.

About 10% of all ALS patients are familial cases, of which 20% have mutations in the superoxide dismutase 1 (SOD 1) gene (formerly known as Cu,Zn-SOD), suggesting that an abnormally functioning Cu,Zn-SOD enzyme may play a pivotal role in the pathogenesis and progression of familial amyotrophic lateral sclerosis (FALS). It is believed that the increased generation of oxygen free radicals, especially hydroxyl radicals, by mutant SOD1, to be the initiating factor that results in the sequence of events leading to motor neuron death in FALS. This hypothesis is supported by recent reports that transfection of neuronal precursor cells with mutant SOD1 results in increased production of hydroxyl radicals and enhanced rate of cell death by apoptosis. Furthermore, applicants believe that oxidative stress is responsible motor neuron death in sporadic forms of ALS as well.

Recent research has revealed that a likely inciting event in the premature neuronal death that is associated with ALS is the presence of mutated mitochondrial genes (mitochondrial DNA, mtDNA). These mtDNA mutations lead to abnormalities in functioning of energy production pathways in mitochondria, resulting in an excessive generation of damaging oxygen derivatives known as "reactive oxygen species" (ROS), including entities called "oxygen free radicals." When ROS production exceeds the capacity of cellular mechanisms to remove/inactivate ROS, the condition known as "oxidative stress" exists.

Oxidative stress can damage many cellular components. Work by the inventor has shown that a critical cell component damaged by oxidative stress in cell models of AD and PD is a particular mitochondrial protein complex known as the "mitochondrial transition pore complex" (MTPC). Normal activity of the MTPC is essential for the maintenance of a bioelectric potential ($\Delta\Psi$) across mitochondrial membranes, which in turn is used for mitochondrial synthesis of energy storage chemicals such as ATP. Loss of $\Delta\Psi$ results in depolarization of mitochondria and initiates a cascade of biochemical reactions which ultimately result in cell death by a mechanism known as "programmed cell death" or "apoptosis." Apoptosis mechanisms have been observed not only in AD and PD, but also in other NDD such as amyotrophic lateral sclerosis (ALS) and Huntington's disease.

Accordingly, one strategy for treating these various neurodegenerative diseases involves the administration of a neuroprotective agent. Effective neuroprotective agents for these debilitating and fatal illnesses should not only be effective in cell culture and animal models of these diseases, but must be tolerated chronically in high enough doses to achieve therapeutic levels in nervous tissues. Ideally such agents would also target cellular components involved in control of cell death pathways and interrupt disease pathophysiology.

In accordance with one embodiment of the present invention a method is provided for treating a neurodegenerative disease such as ALS. The method comprises the steps of administering pramipexole to the individual in an amount effective to reduce oxidative stress in that individual.

Pramipexole (PPX, 2-amino-4,5,6,7-tetrahydro-6-propylaminobenzathiazole) exists as two sterioisomers:

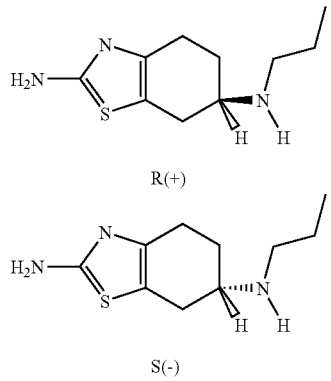

The S(−) enantiomer is a potent agonist at D2 family dopamine receptors and is extensively used in the symptomatic management of PD. The synthesis, formulation and administration of pramipexole is described in U.S. Pat. Nos. 4,843,086, 4,886,812 and 5,112,842, the disclosures of which are incorporated herein. S (−) PPX has been shown by several groups to be neuroprotective in cellular and animal models of increased oxidative stress, including MPTP toxicity to dopamine neurons (see U.S. Pat. Nos. 560,420 and 6,156,777, the disclosures of which are incorporated herein). S(−) PPX reduces oxidative stress produced by the parkinsonian neurotoxin and ETC complex I inhibitor methylpyridinium (MPP+) both in vitro and in vivo and can block opening of the mitochondrial transition pore (MTP) induced by MPP+ and other stimuli (Cassarino, et al, 1998). The lipophilic cationic structure of PPX is suggestive of the possibility that concentration into mitochondria across $\Delta\Psi_M$, in combination with its low reduction potential (320 mV), may account for these desirable neuroprotective properties.

Dosing with S(−) PPX is limited in humans by its potent dopamine agonist properties and will restrict achievable brain drug levels. Because the R(+) enantiomer of PPX has very little dopamine agonist activity (Schneider and Mierau, J Med Chem 30:494–498,1987) but may retain the desirable molecular/antioxidant properties of S(−) PPX, this compound is suggested herein as having utility as an effective inhibitor of the activation of cell death cascades and loss of viability that occurs in neurodegenerative diseases.

SUMMARY OF THE INVENTION

The present invention provides methods for preventing and/or delaying symptoms, or alleviating symptoms relating to a wide variety of neurodegenerative diseases. More particularly, the invention is directed to compositions comprising pramipexole and methods of using such compositions to treat amyotrophic lateral sclerosis (ALS).

BRIEF DESCRIPTION OF THE DRAWINGS

In FIG. 1A, cells were homogenized in isotonic sucrose, centrifuged, and 100 μg of supernatant protein electrophoresed using SDS-PAGE, transferred to nylon membranes and immunostained for cytochrome C with enhanced chemiluminescence detection. The most lefthand band (designated "0hr" on the x axis) corresponds to mitochondrial cytochrome C at time "0", and the other bands represent electrophoresed cytoplasmic protein immunostained for cytochrome C. Positions of MW markers are shown on the y axis. Other batches of cells were assayed for caspase 3 using a commercial system, according to manufacturer's instructions (Biomol). Caspase assays shown in FIG. 1B are the results of 3–4 independent experiments. *$p<0.05$ compared to activity at 0.25 hrs.

FIG. 5 is a graphic representation of the time course of changes in serum 2,3-DHBA levels in ALS and control (CTL) subjects after administration of 1.3 grams of aspirin.

FIG. 6 is a graphic representation of the effect of pramipexole on serum 2,3-DHBA concentration.

DETAILED DESCRIPTION OF THE INVENTION

Definitions

Figure 1A:
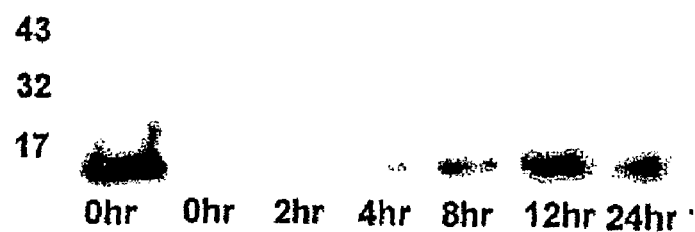
FIG. 1A represents a time course of MPP+-induced release of cytochrome C and FIG. 1B represents a time course of MPP+-induced activation of caspase 3. SH-SY5Y cells were incubated with 5 mM MPP+ for varying times and harvested.

In describing and claiming the invention, the following terminology will be used in accordance with the definitions set forth below.

As used herein, the term "purified" and like terms relate to the isolation of a molecule or compound in a form that is substantially free of contaminants normally associated with the molecule or compound in a native or natural environment.

As used herein, the term "treating" includes prophylaxis of the specific disorder or condition, or alleviation of the symptoms associated with a specific disorder or condition and/or preventing or eliminating said symptoms.

As used herein, an "effective amount" means an amount sufficient to produce a selected effect. For example, effective amount of of pramipexole or derivative thereof encompasses an amount that will inhibit the generation of or decrease the levels of reactive oxygen species present in an individual.

As used herein, the term "halogen" means Cl, Br, F, and I. Especially preferred halogens include Cl, Br, and F. The term "haloalkyl" as used herein refers to a $C_1-C_4$ alkyl radical bearing at least one halogen substituent, for example, chloromethyl, fluoroethyl or trifluoromethyl and the like.

The term "$C_1-C_n$ alkyl" wherein n is an integer, as used herein, represents a branched or linear alkyl group having from one to the specified number of carbon atoms. Typically $C_1-C_6$ alkyl groups include, but are not limited to, methyl, ethyl, n-propyl, iso-propyl, butyl, iso-butyl, sec-butyl, tert-butyl, pentyl, hexyl and the like.

The term "$C_2-C_n$ alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "$C_2-C_n$ alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

The term "$C_3-C_n$ cycloalkyl" wherein n=8, represents cyclopropyl, cyclobutyl, cyclopentyl, cyclohexyl, cycloheptyl, and cyclooctyl.

As used herein the term "aryl" refers to a mono- or bicyclic carbocyclic ring system having one or two aromatic rings including, but not limited to, phenyl, benzyl, naphthyl, tetrahydronaphthyl, indanyl, indenyl, and the like. The term ($C_5-C_8$ alkyl)aryl refers to any aryl group which is attached to the parent moiety via the alkyl group.

The term "heterocyclic group" refers to a mono- or bicyclic carbocyclic ring system containing from one to three heteroatoms wherein the heteroatoms are selected from the group consisting of oxygen, sulfur, and nitrogen.

As used herein the term "heteroaryl" refers to a mono- or bicyclic carbocyclic ring system having one or two aromatic rings containing from one to three heteroatoms and includes, but is not limited to, furyl, thienyl, pyridyl and the like.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The compounds encompassed by the present invention include compounds that contain one or more asymmetric centers in the molecule. In accordance with the present invention a structure that does not designate the stereochemistry is to be understood as embracing all the various optical isomers, as well as racemic mixtures thereof.

As used herein, the term neuroprotective agent refers to an agent that prevents or slows the progression of neuronal degeneration and/or prevents neuronal cell death.

The Invention

The present invention is directed to the use of tetrahydrobenthiazoles to treat neurodegenerative diseases, including ALS. More particularly, the tetrahydrobenthiazoles of the present invention have the general structure:

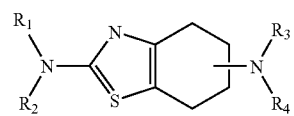

I wherein $R_1$, $R_2$, $R_3$, and $R_4$, are independently selected from the group consisting of H, $C_1-C_3$ alkyl and $C_1-C_3$ alkene. In one preferred embodiment the $NR_3R_4$ group is in the 6-position. In another embodiment $R_1$, $R_2$ and $R_4$, are H, $R_3$ is $C_1-C_3$ alkyl, and the $NR_3R_4$ group is in the 6-position. In one embodiment the compound has the general structure of formula I, wherein $R_1$ and $R_2$ are each H and $R_3$, and $R_4$ are H or $C_1-C_3$ alkyl.

In accordance with one embodiment, the present invention is directed to a method of treating ALS. The method comprises administering to a patient a compound having the general structure:

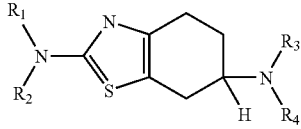

wherein $R_1$ and $R_2$ are H, and $R_3$, and $R_4$, are H, or $C_1-C_3$ alkyl. In one preferred embodiment $R_1$, $R_2$ and $R_4$, are H, and $R_3$ is propyl. In another embodiment, the composition comprises pramipexole wherein pramipexole component consists essentially of one of the two sterioisomers of pramipexole (either R(+)-2-amino-4,5,6,7-tetrahydro-6-propylaminobenzathiazole or S(-)-2-amino-4,5,6,7-tetrahydro-6-propylaminobenzathiazole). In one embodiment the active agent of the composition consists of the pramipexole sterioisomer, R(+)-2-amino-4,5,6,7-tetrahydro-6-propylaminobenzathiazole dihydrochloride, or other pharmacologically acceptable salts, substantially free of its S(−) enantiomer. In one embodiment a composition is provided wherein greater than 80% of the pramipexole compounds present in the composition are in the R(+) conformation, and more preferably greater than 90% or greater than 95% of the pramipexole compounds are in the R(+) conformation. In one embodiment a composition comprising pramipexole is provided wherein greater than 99% of the pramipexole compounds are in the R(+) conformation.

In one embodiment a composition is provided that comprises an active agent consisting essentially of R(+)-2-amino-4,5,6,7-tetrahydro-6-propylaminobenzathiazole dihydrochloride, or other pharmacologically acceptable salts thereof, and a phamaceutically acceptable carrier. This composition can be administered orally on a chronic basis for preventing neural cell loss in NDD (and more particularly reducing oxidative stress in ALS patients), or it can be formulated and administered intravenously for prevention of neural cell loss in acute brain injury.

The neuroprotective effect of the compositions of present invention derives at least in part from the active compound's ability to prevent neural cell death by at least one of three mechanisms. First, the present tetrahydrobenzthiazoles are capable of reducing the formation of ROS (both in vivo in rat brain and in vitro in cells with impaired mitochondrial energy production) induced with neurotoxins that can mimic PD. In this manner the tetrahydrobenzthiazoles function as "free radical scavengers." Second, the tetrahydrobenzthiazoles can partially restore the reduced $\Delta\Psi$ that is correlated with AD and PD mitochondria. Third, tetrahydrobenzthiazoles can block the apoptotic cell death pathways which are produced by pharmacological models of AD and PD mitochondrial impairment.

In accordance with one embodiment a method is provided for reducing oxidative stress in an ALS patient. A reduction in oxidative stress, for the purposes of the present invention, is intended to include any reduction in the level of reactive oxygen species present in the patient, including for example, decreased serum ROS levels as detected by the conversion of salicylate to 2,3 DHBA. The method comprises administering an effective amount of a tetrahydrobenzthiazole having the general formula:

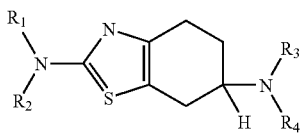

wherein $R_1$, $R_2$ and $R_4$, are H, and $R_3$ is $C_1$–$C_3$ alkyl. In one embodiment, the tetrahydrobenzthiazole is R(+)-2-amino-4,5,6,7-tetrahydro-6-propylaminobenzathiazole or S(−)-2-amino-4,5,6,7-tetrahydro-6-propylaminobenzathiazole or a racemic mixture of the R(+) and S(−) sterioisomers. The amount of tetrahydrobenzthiazole administered to treat ALS will vary based on route of administration, as well as additional factors including the age, weight, general state of health, severity of the symptoms, frequency of the treatment and whether additional pharmaceuticals accompany the treatment. The dosage amount of the active compound to be administered is easily determined by routine procedures known to those of ordinary skill in the art.

Alternatively, the present invention provides a method for enhancing the bioelectric potential ($\Psi$) across mitochondrial membranes of cells with impaired mitochondrial energy production. The method comprises the steps of contacting cells having impaired mitochondrial energy production with a composition comprising a pramipexole active agent and a pharmaceutically acceptable carrier. In one embodiment the pramipexole active agent consists essentially of the R(+) 2-amino-4,5,6,7-tetrahydro-6-propylaminobenzathiazole sterioisomer and the pharmacologically acceptable salts thereof.

A number of central nervous system diseases and conditions result in neuronal damage and each of these conditions can be treated with the tetrahydrobenzthiazole compositions of the present invention. Conditions which can lead to nerve damage include: Primary neurogenerative disease; Huntington's Chorea; Stroke and other hypoxic or ischemic processes; neurotrauma; metabolically induced neurological damage; sequelae from cerebral seizures; hemorrhagic stroke; secondary neurodegenerative disease (metabolic or toxic); Parkinson's disease, Alzheimer's disease, Senile Dementia of Alzheimer's Type (SDAT); age associated cognitive dysfunctions; or vascular dementia, multi-infarct dementia, Lewy body dementia, or neurogenerative dementia.

The invention is also safe to administer to humans. S(−) pramipexole, which is a potent dopamine agonist approved for the treatment of PD symptoms is the enantiomer of R(+) pramipexole. However, R(+) pramipexole lacks pharmacological dopamine activity. Accordingly, R(+) 2-amino-4,5,6,7-tetrahydro-6-propylaminobenzathiazole and the pharmacologically acceptable salts thereof can be administered in much larger doses than S(−) pramipexole and can achieve brain levels capable of providing neuroprotection. In accordance with one embodiment ALS is treated by administering either R(+) or R(−) pramipexole, however the administration of R(+) 2-amino-4,5,6,7-tetrahydro-6-propylaminobenzathiazole is preferred because much higher doses can be given. As indicated in Example 1, the S(−) and R(+) isomers are approximately equipotent in reducing oxidative stress. However the use of the R(+) isomer allows one to administer higher doses and thus achieve greater reduction in toxic oxygen free radicals. Accordingly, in one embodiment a method of reducing neural cell death in patients with amyotrophic lateral sclerosis (ALS) is provided, wherein the patient is administered a pharmaceutical composition comprising a compound of the general structure:

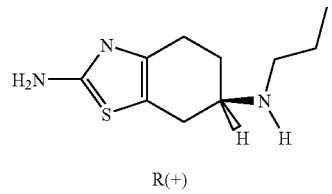

R(+)

The synthesis of Pramipexole is described in European Patent 186 087 and its counterpart, U.S. Pat. No. 4,886,812, the disclosure of which is incorporated herein.

In one embodiment, pramipexole, and more preferably R(+)-2-amino-4,5,6,7-tetrahydro-6-propylaminobenzathiazole is compounded with binding agents to yield tablets for oral administration, or with substances known to the art to yield a transdermal patch ("skin patch") for continuous delivery. Alternatively, pramipexole can be formulated with the necessary stabilizing agents to produce a solution that can be administered parenterally (ie, intravenously, intramuscularly, subcutaneously). The oral and/or transdermal preparations of the invention are used to reduce neural cell death in patients with NDD (ie Alzheimer's disease, Parkinson's disease, Huntington's disease, amyotrophic lateral sclerosis). The parenteral formulations of the invention are used to reduce neural cell death in patients with acute brain injury (ie. stroke, sub-arachnoid hemorrhage, hypoxic-ischemic brain injury, status epilepticus, traumatic brain injury, hypoglycemic brain injury).

The use of R(+) pramipexole to treat NDD, by virtue of its being a relatively inactive stereoisomer of the dopamine agonist S(−) pramipexole (Mirapex, Pharmacia and Upjohn), solves an important problem associated with the use of S(−) pramipexole as a dopamine agonist. Dosing of Mirapex is limited by dopaminergic side effects on blood pressure and mentation. R(+)-2-amino-4,5,6,7-tetrahydro-6-propylaminobenzathiazole has 1% or less of the potency to produce the side effects that result from the use of S(−) pramipexole. Thus, the present invention can be administered more safely to AD patients, who are typically intolerant of even small doses of dopamine agonist medication. Also the present invention can be administered intravenously in much larger doses than S(−) pramipexole. Thus, it can safely be used in conditions such as stroke, where lowering of blood pressure can be detrimental.

In one embodiment a method for treating a patient having a neurodegenerative disease is provided, that simultaneously reduces the risk of dopaminergic side effects. The method comprises the step of administering a composition comprising a pramipexole active agent and a phamaceutically acceptable carrier, wherein the pramipexole active agent consists essentially of the R(+) 2-amino-4,5,6,7-tetrahydro-6-propylaminobenzathiazole sterioisomer and the pharmacologically acceptable salts thereof. In one embodiment the neurodegenerative disease to be treated is selected from the group consisting of ALS, Alzheimer's disease and Parkinson's disease, and the composition is administered at a dosage of about 10 mg to about 500 mg per day of R(+) 2-amino-4,5,6,7-tetrahydro-6-propylaminobenzathiazole or the pharmacologically acceptable salts thereof.

The dosage to be used is, of course, dependent on the specific disorder to be treated, as well as additional factors including the age, weight, general state of health, severity of the symptoms, frequency of the treatment and whether additional pharmaceuticals accompany the treatment. The amounts of the individual active compounds are easily determined by routine procedures known to those of ordinary skill in the art. For example, the tetrahydrobenzthiazoles of the present invention can be administered orally to humans with NDD in daily total doses between 10 mg and 500 mg. Alternatively, the tetrahydrobenzthiazoles can be administered parenterally to humans with acute brain injury in single doses between 10 mg and 100 mg, and/or by continuous intravenous infusions between 10 mg/day and 500 mg/day.

In one preferred embodiment, R(+) 2-amino-4,5,6,7-tetrahydro-6-propylaminobenzathiazole (or a pharmacologically acceptable salts thereof) is administered to a patient suffering from a neurogenerative disease such as ALS to treat the disease. As used herein, the term "treating" includes alleviation of the symptoms associated with a specific disorder or condition and/or preventing or eliminating said symptoms. More particularly, a composition comprising a pramipexole active agent and a pharmaceutically acceptable carrier is administered to the patient to prevent or substantially reduce neural cell death, wherein the pramipexole active agent consists essentially of the R(+) 2-amino-4,5,6,7-tetrahydro-6-propylaminobenzathiazole (and the pharmacologically acceptable salts thereof) sterioisomer of pramipexole. The synthesis, formulation and administration of pramipexole is described in U.S. Pat. Nos. 4,843,086; 4,886,812; and 5,112,842; which are incorporated by reference herein.

Hydroxyl radical generation in the tissues of an individual results in an increase in the conversion of salicylate to 2,3 dihydroxybenzoic acid (DHBA) (Floyd et al. (1984) J. Biochem. Biophys. Methods 10:221–235; Hall et al. (1993) J. Neurochem. 60:588–594). Thus the accumulation of 2,3 DHBA in the serum of individuals can be used as an indicator of level of oxidative stress suffered by that individual. The effect of R(+) 2-amino-4,5,6,7-tetrahydro-6-propylaminobenzathiazole or S(−) 2-amino-4,5,6,7-tetrahydro-6-propylaminobenzathiazole on 2,3 dihydroxybenzoic acid (DHBA) serum levels was investigated. As is shown in FIGS. 5 and 6, individual serum levels of 2,3 DHBA decreased in ALS patients after treatment with S(−) 2-amino-4,5,6,7-tetrahydro-6-propylaminobenzathiazole. These data demonstrate that treatment with pramipexole lowers oxidative stress in vivo in ALS patients.

Figure 7:
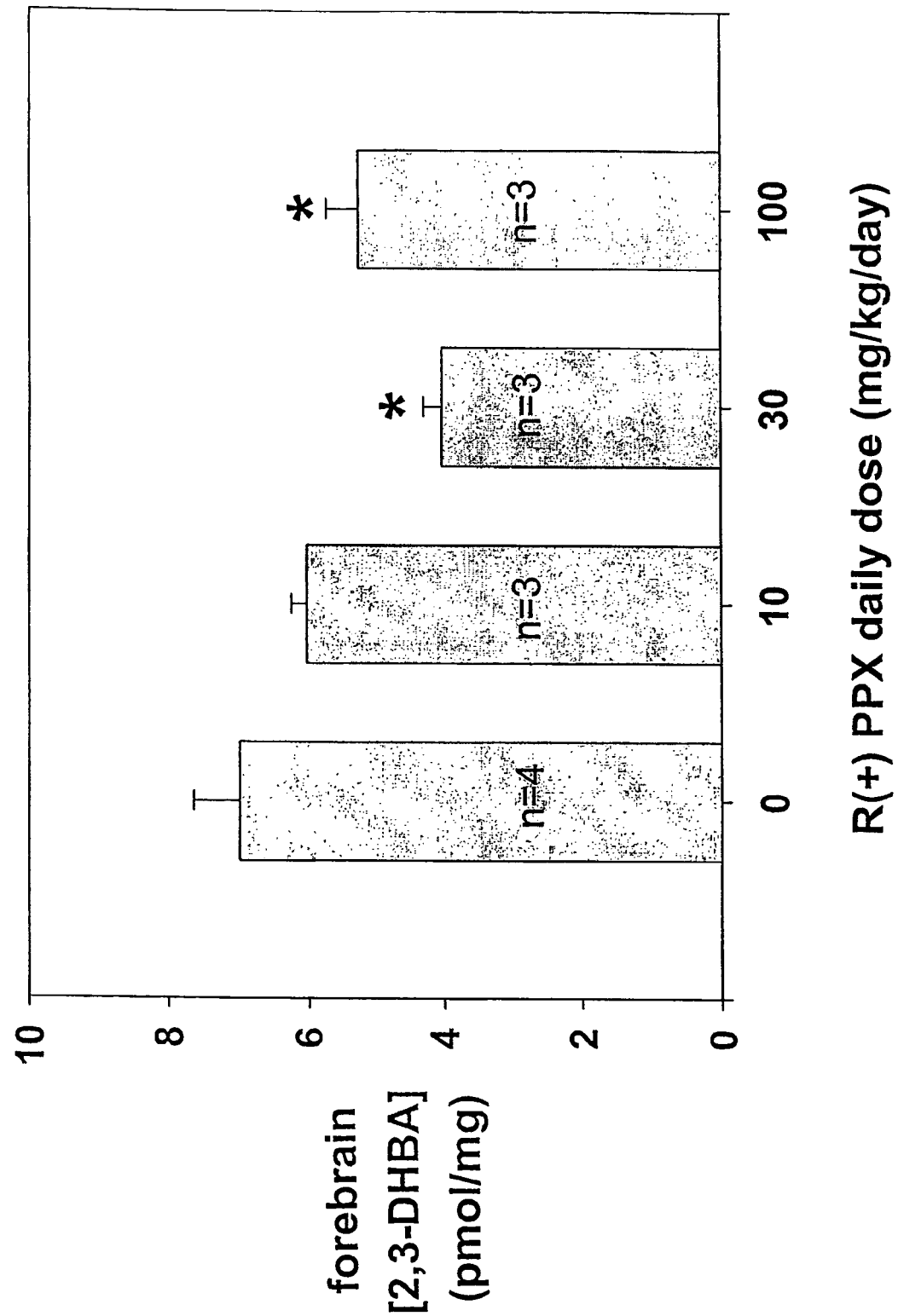
FIG. 7. Mice were adminstered R(+) PPX in their drinking water and then treated with a neurotoxin (N-methyl-4-pheny-1,2,3,6-tetrahydropyridine, MPTP) which increases oxidative stress in the brain and forebrain 2,3-DHBA levels were determined.

Furthermore, as shown in FIG. 7 additional studies were conducted on mice and demonstrate the effectiveness of pramipexole in reducing oxidative stress in vivo. In this study mice were administered R(+) PPX in their drinking water for 8 weeks at 3 different daily doses, and then were given a neurotoxin (N-methyl-4-pheny-1,2,3,6-tetrahydropyridine, MPTP) which increases oxidative stress in the brain. Brain tissue was then analyzed for oxygen free radical production. The data show that the 30 mg/kg/day and 100 mg/kg/day doses resulted in significant reduced free radical levels in the brain.

Toxicology studies have also been conducted and no evidence of adverse effects were detected. In particular, an 8 week toxicology study was performed in the mice given R(+) PPX in their drinking water. All their major organs were examined pathologically and no lesions were found. While this does not address the issue of effectiveness of R(+) PPX as a neuroprotectant, it does demonstrate the potential safety (and thus feasibility) of administering very high doses of the drug to humans chronically.

The present invention is also directed to pharmaceutical compositions comprising the tetrahydrobenzthiazole compounds of the present invention. More particularly, the tetrahydrobenzthiazole compounds can be formulated as pharmaceutical compositions using standard pharmaceutically acceptable carriers, fillers, solublizing agents and stabilizers known to those skilled in the art.

Pharmaceutical compositions comprising the tetrahydrobenzthiazoles are administered to an individual in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

The invention also provides a pharmaceutical pack or kit comprising one or more containers filled with one or more of the ingredients of the pharmaceutical compositions of the invention. In accordance with one embodiment a kit is provided for treating an ALS patient. In this embodiment the kit comprises one or more of the tetrahydrobenzthiazoles of the present invention, and more particularly the R(+) 2-amino-4,5,6,7-tetrahydro-6-propylaminobenzathiazole sterioisomer.

These pharmaceuticals can be packaged in a variety of containers, e.g., vials, tubes, microtiter well plates, bottles, and the like. Preferably, the kit will also include instructions for use.

EXAMPLE 1

R(+) and S(−) PPX are Effective Inhibitors of Activation of Cell Death Cascades.

Materials and Methods

Cell culture

SH-SY5Y human neuroblastoma cells were obtained from the American Tissue Culture Collection (www.atcc.org) and maintained in culture in a replicating state. For caspase assays and cytochrome C release studies they were grown in T75 flasks with DMEM/high glucose containing 10% fetal bovine serum, antibiotic/antimicotic (100 IU/ml of penicillin, 100 µg/ml of streptomycin sulfate, 0.25 µg/ml of amphotericin B) and 50 µg/ml of uridine and 100 µg/ml of pyruvate in a 5% $CO_2$ atmosphere at 37° C. to approximately full confluence ($2 \times 10^7$ cell/flask). They were then incubated with 5 mM methylpyridinium iodide (MPP+; Sigma; www.sigma-aldrich.com) or 100 µM 25–35 or 35–25 beta amyioid peptides (Bachem; www.bachem.com) for varying times, then harvested. For cell death studies, the cells were plated into 96 well black-bottom plates and grown for 24 hours in DMEM media before being exposed to toxin.

Caspase Assays

After exposure to MPP+ or beta amyloid peptide, cells were collected in PBS and centrifuged at 450×g for 6 minutes at 4° C. Cell pellets were resuspended in a hypotonic cell lysis buffer [25 mM HEPES, 5 mM $MgCl_2$, 5 mM EDTA, 1M DTT and protease inhibitor cocktail (Sigma Chemical)] at a concentration of $2 \times 10^7$ cells/100 µl of lysis buffer. Lysates were subjected to four cycles of freezing and thawing. Cell lysates were then centrifuged at 16,000×g for 30 minutes at 4° C. The supernatant fractions were collected, and protein content was measured by Lowry assay (Bio-Rad). 100 µg of protein was used to measure caspase activity in 96 well plates and was assayed in quadruplicate. The activity was measured using the assay buffer and the protocol provided by the manufacturers. (Biomol, caspase 3; Promega, caspases 3 and 9). Caspase activity is based on cleavage of synthetic peptide substrates resulting in liberation of colored (p-nitroaniline (p-NA), Biomol) or fluorescent (aminomethylcoumarin (AMC), Promega) chromogens. Only activated caspases are capable of cleaving these substrates, and chromogen generation is completely inhibited when the caspase inhibitor provided with each assay kit is included in the assay. Under the indicated assay conditions linear rates of generation of chromogen were observed over 2 hours. Chromogen absorbance (p-NA) was measured on an OptiMax plate reader or chromogen fluorescence (AMC) on a SpectraMax Gemini plate reader at zero time and after 30 minutes of incubation at 37 degrees to estimate relative caspase activities. Chromogen signal at zero time was subtracted from the readings at 30 minutes.

Cell Death

Cell death was estimated by measuring loss of calcein retention with the "Live-Dead" assay (Molecular Probes; www.molecularprobes.com) in cells grown in 96 well plates and incubated with calcein-AM, according to manufacturer's instructions. Calcein signals were assayed in a SpectraMax Gemini adjustable fluorescent plate reader (Molecular Devices). Calcein fluorescence from cells preincubated with methanol was subtracted from all readings as background. Each assay was performed with 8 wells/condition, which were averaged. 3–8 independent experiments were performed to evaluate a broad range of concentrations of S(−) and R(+) PPX in this paradigm.

Cytochrome C Western Blot

Cytochrome C was detected by Western blot following polyacrylamide electrophoresis of 100 µg of cell supernatant protein and transfer to nylon membrane.

The primary antibody was a mouse monoclonal anti-cytochrome C, obtained from Pharmingen and used at 1:10,000 dilution. Detection was performed with enhanced chemiluminescence (Pierce) and imaged on a BioRad FluorS imaging station.

Drugs

R(+) and S(−) PPX (gifts of Pharmacia Corporation) were obtained as their dihydrochloride salts and dissolved directly into culture media. Bongkreckic acid, an antagonist of the ATP binding site on the adenine nucleotide translocator, was provided as a solution in 1M $NH_4OH$. Aristolochic acid (sodium salt), a phospholipase A2 inhibitor, was obtained from Sigma Chemical Co. In the caspase experiments, drugs were added 1 hour before MPP+ or beta amyloid peptide. In the calcein/cell death experiments, drugs were added 4 hours before MPP+.

Results

Activation of caspases by MPP+ and BA 25–35

Figure 1B:
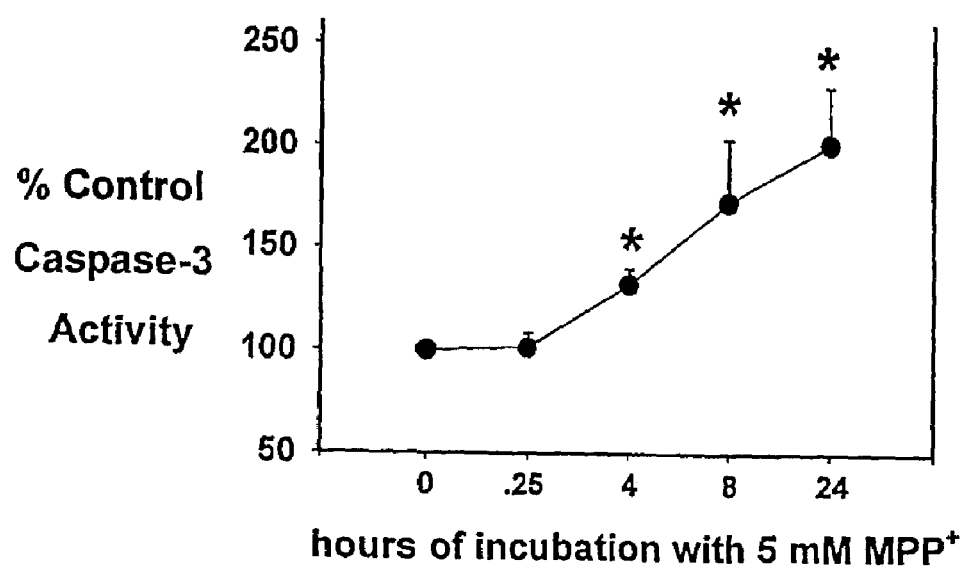

FIG. 1B shows the time course of caspase 3 activity during incubation of SH SY5Y cells with 5 mM MPP+. Increased activity was detectable by 4 hours and had increased about 2-fold by 24 hours. FIG. 1A shows the Western blot result for cytochrome C protein released into cytoplasm. Similar to the biochemical activity curve, cytoplasmic cytochrome C is detectable in small amounts by 4 hours and increases substantially by 12 hours.

Figure 2:
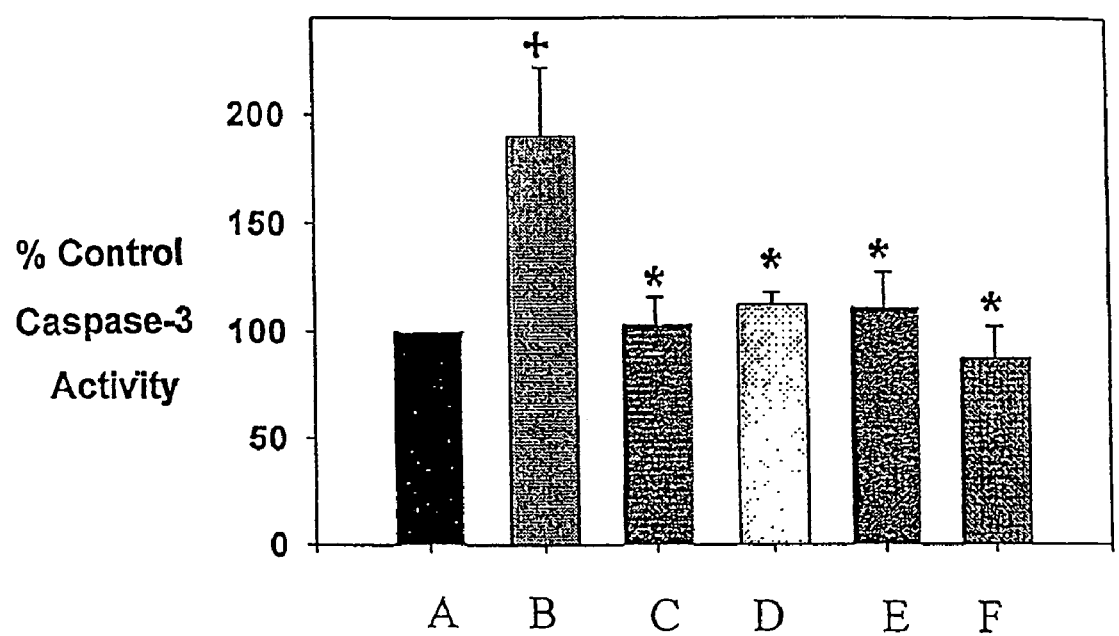
FIG. 2 represents data showing the inhibition of MPP+-induced caspase 3 activation by PPX, bongkreckic acid and aristolochic acid. SH-SY5Y cells were incubated with 5 mM MPP+ for 24 hours in the absence of or presence of 1 mM S(−) PPX, 1 mM R(+) PPX, 250 μM bongkreckic acid (BKA) or 25 μM aristolochic acid (ARA) or combinations thereof. Cells were then assayed for caspase 3 activity. Shown in FIG. 2 are the mean +/−SEM for 4–5 independent experiments. Lanes A-F represent caspase 3 activation by cells incubated with the following compounds: A, control (no compounds added); B, MPP+; C, MPP+/BKA; D, MPP+/S(−) PPX; E, MPP+/R(+) PPX; F, MPP+/ARA. For lanes B, $p<0.05$ compared to control; and for lanes C—F, $p<0.05$ compared to MPP+treated cells (lane B).

FIG. 2 shows that both R(+) and S(−) PPX enantiomers suppressed caspase 3 activation during MPP+exposure. MPP+-induced increases in caspase 3 activity were also blocked by bongkreckic acid, a specific antagonist of the ATP binding site on the inner membrane site of the adenine nucleotide translocator.

Figure 3:
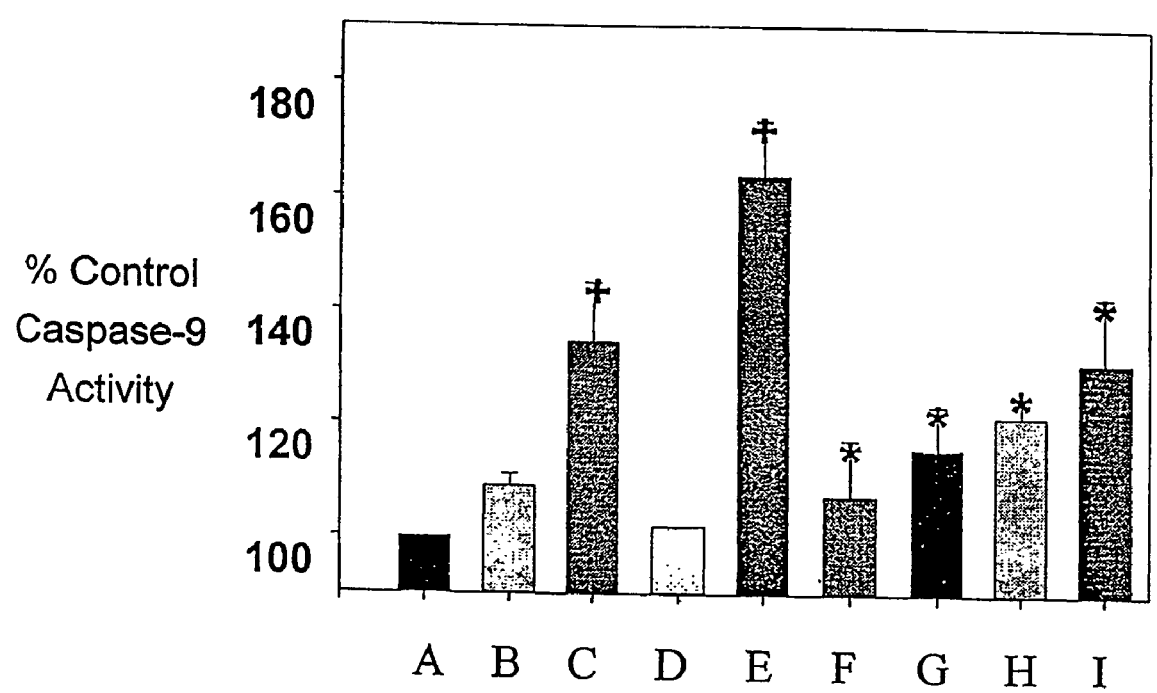
FIG. 3 represents data showing the inhibition of MPP+-induced caspase 9 activation by PPX, bongkreckic acid and aristolochic acid. SH-SY5Y cells were incubated with 5 mM MPP+ for 4 or 8 hours in the absence of or presence of 1 mM S(−) PPX, 1 mM R(+) PPX, 250 μM bongkreckic acid (BKA) or 25 μM aristolochic acid (ARA). Cells were then assayed for caspase 9 activity. Shown in FIG. 3 are the mean +/−SEM for 3–4 independent experiments. Lanes A–I represent caspase 9 activation by cells incubated with the following compounds: A, control (no compounds added); B, 15 min MPP+; C, 4 hr MPP+; D, 4 hr MPP+/PPX; E, 8 hr MPP+; F, 8 hr MPP+/BKA; G, 8 hr MPP+/S(−) PPX; H, 8 hr MPP+/R(+) PPX; I, 8 hr MPP+/ARA. For lanes C and E, $p<0.01$ compared to control; and for lanes F, G, H, and I $p<0.05$ compared to control.

Aristolochic acid, a phospholipase A2 inhibitor, previously shown to block MPP+-induced apoptosis of SH-SY5Y cells (Fall and Bennett, 1998), also prevented increases in caspase 3 activity. Activation of caspases by MPP+ and BA 25–35 peptide was blocked by PPX enantiomers and agents active at the mitochondrial transition pore. S(−) PPX reduced by about 70% the increases in caspase 3 activity following incubation with BA 25–35 peptide and had no suppressive effect by itself. MPP+ exposure also increased activity of caspase 9 with a time course similar to activation of caspase 3 (see FIG. 3). The increases in caspase 9 activity were also blocked by S(−) and R(+) PPX, bongkreckic acid and aristolochic acid.

Figure 4A:
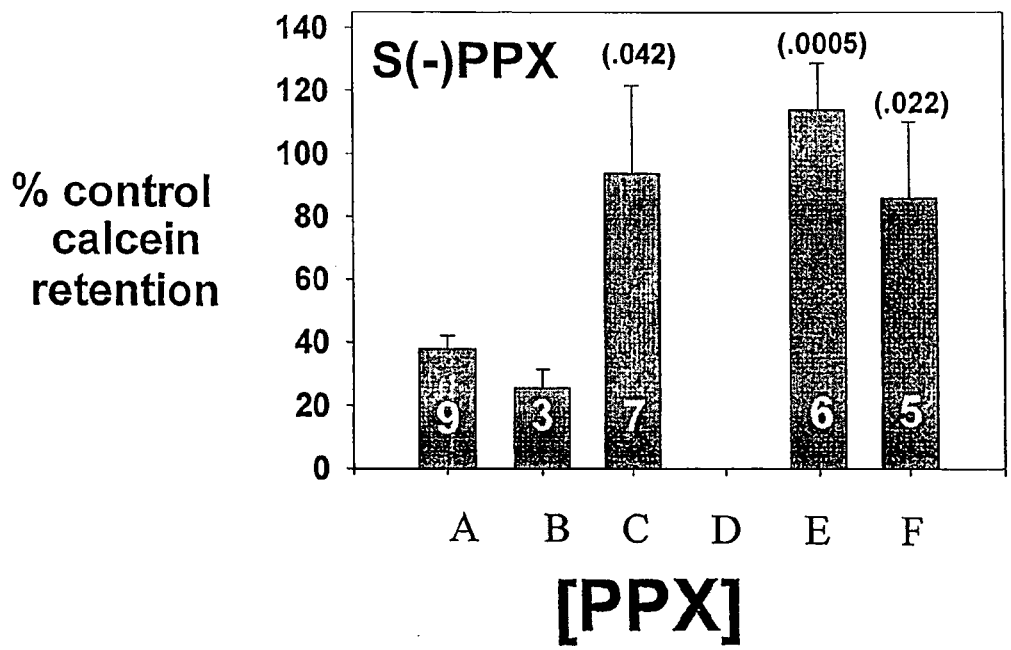
FIGS. 4A & 4B. Inhibition of MPP+-induced cell death by PPX enantiomers. SH-SY5Y cells were incubated with 5 mM MPP+ for 24 hours in the absence of or presence of increasing concentrations of S(−) PPX (FIG. 4A) or R(+) PPX (FIG. 4B). Lanes A–F represent cells treated with 0 nM, 3 nM, 30 nM, 300 nM, 3 uM, and 30 um of PPX, respectively. The cells were then incubated with calcein-AM, washed and read on a fluorescent plate reader. The number of independent experiments is indicated on each bar, and the P values by t-test for comparison to no PPX (MPP+ only) are shown above each bar. In the presence of MPP+, 3 nM, R(+) PPX caused greater calcein retention than S(−) PPX (p=0.035), and 3 μM, S(−) PPX caused greater calcein retention than R(+) PPX (p=0.027).
Figure 4B:
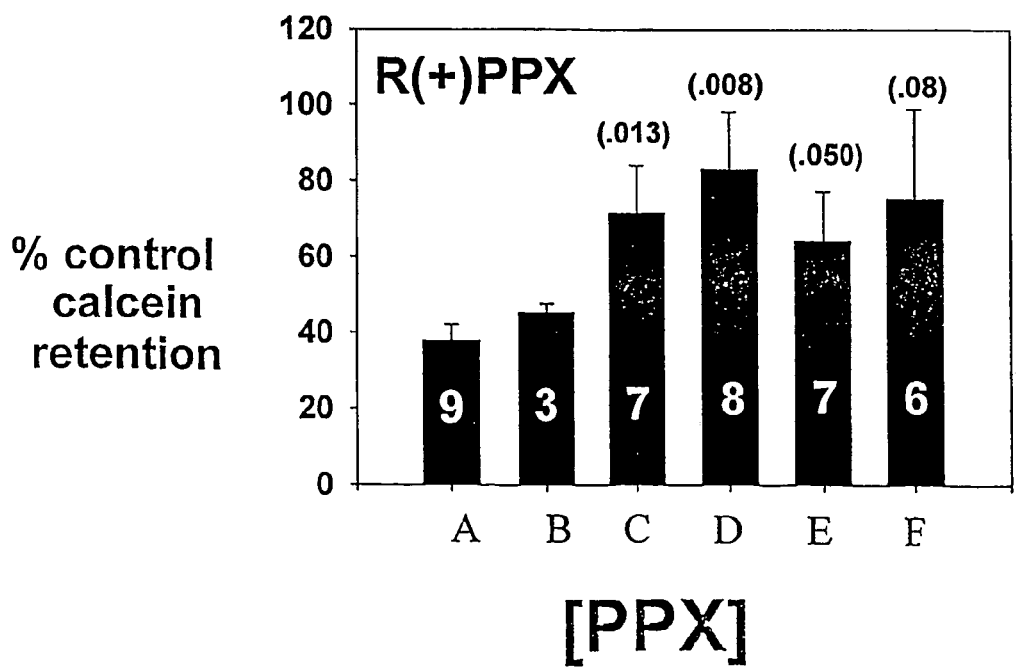

FIG. 4 shows the effects on cellular calcein retention of incubating SH-SY5Y cells with varying concentrations of R(+) or S(−) PPX prior to exposure to 5 mM MPP+ for 24 hours. Calcein is a fluorescent dye that is retained inside cells as a function of their ability to maintain a plasma membrane potential. MPP+ alone reduced calcein uptake by about 60%. Both PPX enantiomers substantially restored calcein uptake at 30 nM levels, and this protective effect was retained through 30 µM PPX's.

Discussion

This study focused on the use of the neurotoxins MPP+ and 25–35 beta amyloid peptide added to replicating SH-SY5Y neuroblastoma cells as cell culture models for studying potential neuroprotective compounds useful for Parkinson's and Alzheimer's diseases, respectively. SH-SY5Y cells are neoplastic, dividing cells of neuroectodermal origin, not primary neurons. They are mitotic as a result of a Ras mutation, leading to chronic activation of MAPK/ERK signaling. SH-SY5Y cells are relatively insensitive in short-term incubations to MPP+, compared to primary neurons. Applicants have found that 2.5 and 5 mM, but not 1 mM, MPP+ produced apoptotic morphology and DNA pyknotic fragments within 18–24 hours. However, longer incubations with lower concentrations of MPP+ may more closely approximate the in vivo MPTP model of PD in animals, and it has been reported that longer term exposure to lower MPP+ levels still can activate the mitochondrial cell death cascade.

SH-SY5Y cells are also sensitive to beta amyloid peptides. Li, et al (1996) found that serum-starved SH-SY5Y showed extensive DNA nicked end labeling after 3 days exposure to 100 μM beta amyloid 2S–3S and exhibited a concentration-dependent increase in DNA laddering. Beta amyloid peptide-induced activation of caspases has not apparently been described in SH-SY5Y, but several reports have shown caspase activations from exposure to beta amyloid peptides in various primary neuron lines. These include activation of caspases-2, -3 and -6 by the 25–35 analogue in cerebellar granule cells, and caspase-3 in rat primary cortical neurons. Thus, it is not surprising that caspase-3 activity (DEVDase) was observed in SH(−)SY5Y exposed to 100 μM beta amyloid 25–35 but no caspase activation was observed after exposure to the reverse 35–25 sequence.

The focus of the present experiments was to determine if PPX enantiomers can prevent activation of caspases and can promote calcein retention as a marker of cell survival in acute toxin exposure, cell culture models of AD and PD. Activation of both the "initiator" caspase 9 and "executioner" caspase 3 was blocked by both PPX enantiomers in the MPP+model for PD, and activation of caspase 3 was blocked by S(−) PPX in the BA 25-3S model for AD. Both PPX enantiomers at nanomolar levels could promote cell survival in the MPP+ model for PD. Thus, the present findings add to the growing body of work describing the neuroprotective actions of PPX and suggest potential clinical utility of this family of compounds in neurodegenerative diseases.

While this study did not examine the most proximate site of action of PPX, several finding implicate the mitochondrial transition pore complex (MTPC) in these cell models. First, bongkreckic acid, a selective adenine nucleotide translocator antagonist and inhibitor of MTP opening, blocked MPP+ induced activation of both caspases 9 and 3. This would be consistent with MPP+ bringing about MTP opening either directly or through mechanisms that involve oxidative stress. In isolated liver mitochondria MPP+ can bring about a classical MTP opening that is incompletely blocked by free radical scavenging enzymes and is more completely blocked by S(−) PPX. Neurotoxic 25–35 BA peptide can also stimulate MTP opening in isolated mitochondria. Both MPP+ and 2S-35 BA peptide increase oxidative stress in brain microdialysis studies in vivo and in neural cell culture in vitro, and S(−) PPX has been shown to reduce MPP+-induced oxidative stress in vitro and in vivo.

EXAMPLE 2

Use of Pramipexole to Treat ALS

Oxidative abnormalities have been identified both in familial amyotrophic lateral sclerosis (FALS) and the more prevalent sporadic ALS (SALS). 2,3-DHBA is a hydroxylated salicylate byproduct that has been shown to be a reliable in vivo marker of increased free radical activity and is reliably assayed by HPLC. Following the administration of an oral salicylate load, elevated serum levels of 2, 3-dihydroxybenzoic acid (2,3-DHBA) and DHBA/salicylate were observed in SALS subjects. As described herein 12 SALS patients were studied to determine the levels of 2,3-DHBA both before and after treatment with pramipexole.

Methods

Participant Preparation

The present study was conducted in two phases. In the first phase eleven definite SALS subjects who met Airlie House criteria, and 7 controls were studied. These participants underwent aspirin loading with subsequent 2,3-DHBA analysis. After receiving 1.3 grams of aspirin po, blood was drawn 2, 3, and 4 hours later. Serum was separated, frozen and stored at −80 degrees. Aliquots of serum were subsequently coded and blinded for 2,3-DHBA and salicylate assays.

In the second phase, 17 subjects with definte SALS were randomly selected from a clinic population. The subjects received 1.3 grams of aspirin po, and blood was drawn 3 hours later. Following acquisition of these baseline samples, SALS participants began pramipexole therapy. Dosage escalation was performed similar to PD patients with an attempt made to reach 1.5 mg t.i.d.-q.i.d. as the final dose, following a 7 week titration. After each participant was on his/her highest pramipexole dose for three weeks, the aspirin loading study was performed once again. Twelve of the original seventeen SALS subjects could complete the pramipexole escalation phase. Of these all but two were able to reach a pramipexole dosage of 6 mg per day, and all patients obtained at least a dosage of 3 mg per day. Each participant was then offered the opportunity to continue with pramipexole treatment.

Specimen Preparation

Preparation of serum: 0.9 ml of serum at 4° C. was mixed with 0.2 ml of 1 M perchloric acid and centrifuged at 15,000 rpm for 10 minutes in a refrigerated microcentrifuge.

Assay for 2,3-DHBA: 20 uL of supernatant were injected in duplicate onto a C18 "Catecholamine" Adsorbosphere column (Alltech) perfused at 0.6 ml/min with buffer consisting of 125 ml/L acetonitrile, 1.5 gn/L of sodium heptane sulfonate, 3 ml/L triethylamine, 100 mg/L of $Na_2$ EDTA with final pH adjusted to 2.8 with phosphoric acid. Detection utilized a CouloChem II flow-through electrochemical detector (ESA, with the following settings: guard cell=+600 mV; E1=−100 mV; E2=+400 mV). 2,3-DHBA eluted at 10–10.5 minutes under these conditions.

Assay for salicylate: 50 uL of supernatant were injected in duplicate onto a C8 Kromosil HPLC column (Alltech) perfused at 0.8–1.0 ml/min with 70% methanol/30% water/0.5% trifluoroacetic acid. Salicylate eluted at 6–7 minutes under these conditions and was detected by ultraviolet absorption at 315 nM.

Results

Figure 5A:
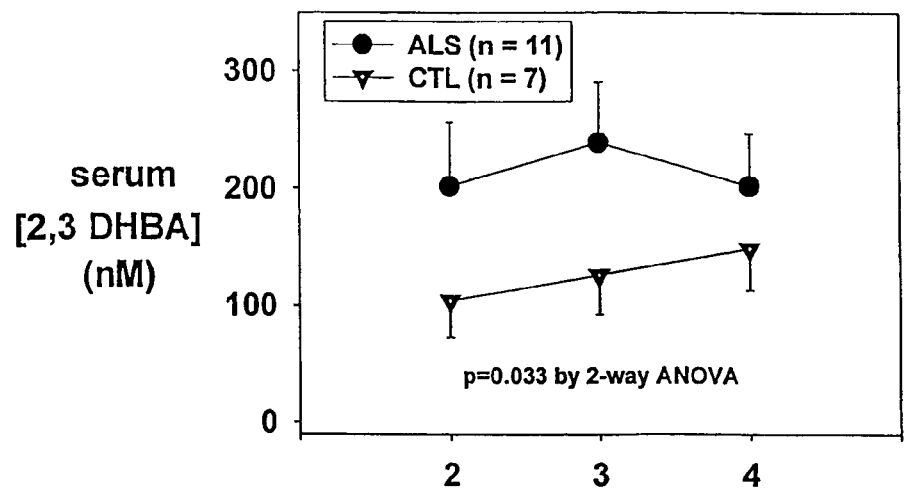
FIG. 5A shows the means +/−SEM for changes in serum 2,3-DHBA concentration.

FIG. 5A shows the time course of increase in 2,3-DHBA serum levels in the 11 SALS (59.2±12.3 yr) and 7 age matched control (56.7±10.7 yr) subjects studied in the first phase. The SALS patients exhibited a range from symptom onset of 10 to 156 months, representing both acute and chronic stages of this disease. Maximum 2,3 DHBA levels were found in SALS subjects at 3 hours after aspirin dosing, and this time point was chosen for the second phase of the study.

In addition, 2-way ANOVA revealed a difference in production of 2,3-DHBA when SALS and control groups were compared across time. This difference was significant at the p=0.033 level for the two populations; post-hoc testing (Tukey test) did not reveal any significant differences between individual time points.

Figure 5B:
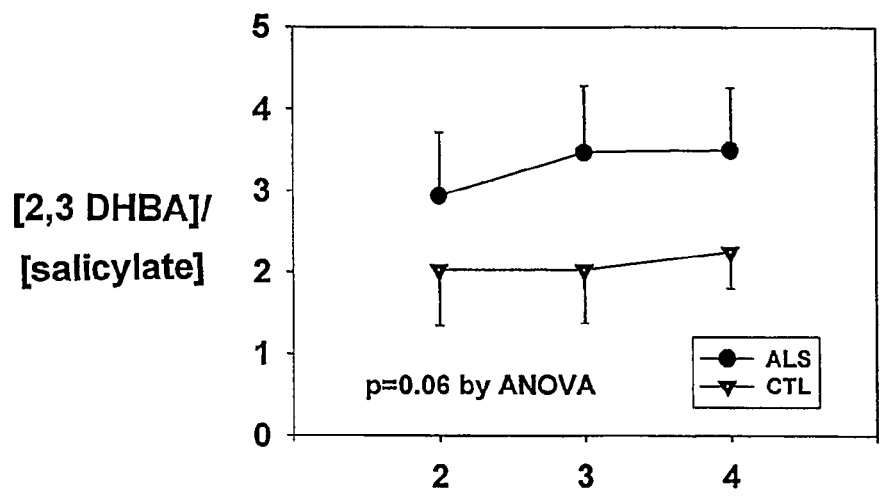
FIG. 5B shows the ratio of serum 2,3-DHBA concentration to salicylate concentration.
Figure 5C:
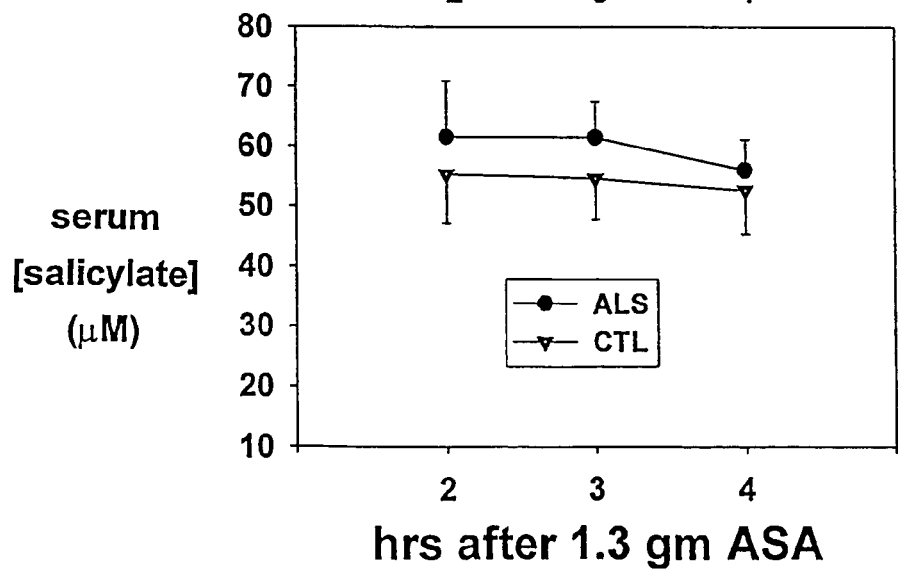
FIG. 5C shows the serum salicylate concentration over the time course.

As an additional comparison, ratios of 2,3-DHBA/salicylate were compared across time for the two populations. The ALS group showed an approximate 1.5-fold increase in this normalized marker of 2,3-DHBA production at 3 hours after administration of aspirin. 2-way ANOVA showed a difference significant at the p=0.06 level (FIG. 5B). Serum salicylate levels were not significantly different over time between the ALS and CTL populations (FIG. 5C). Of the original 17 patients who entered the second phase of the study, 5 dropped out due to complications from the disease or inability to tolerate the medication. The remaining participants consisted of 8 males and 4 females. The average age was 63.2 years. Pramipexole therapy was well tolerated by these ALS subjects. These participants did not exhibit any evidence of clinical dementia, nor did they have significant cardiovascular instability.

The patients enrolled in this study represented various clinical stages of disease progression. Four participants were non-ambulatory, two of which were ventilator-dependant. The other eight were ambulatory at the onset of the study. The average time from the entry into the study and the final blood draw was 76.6 days with a range of 49–105 days.

Figure 6A:
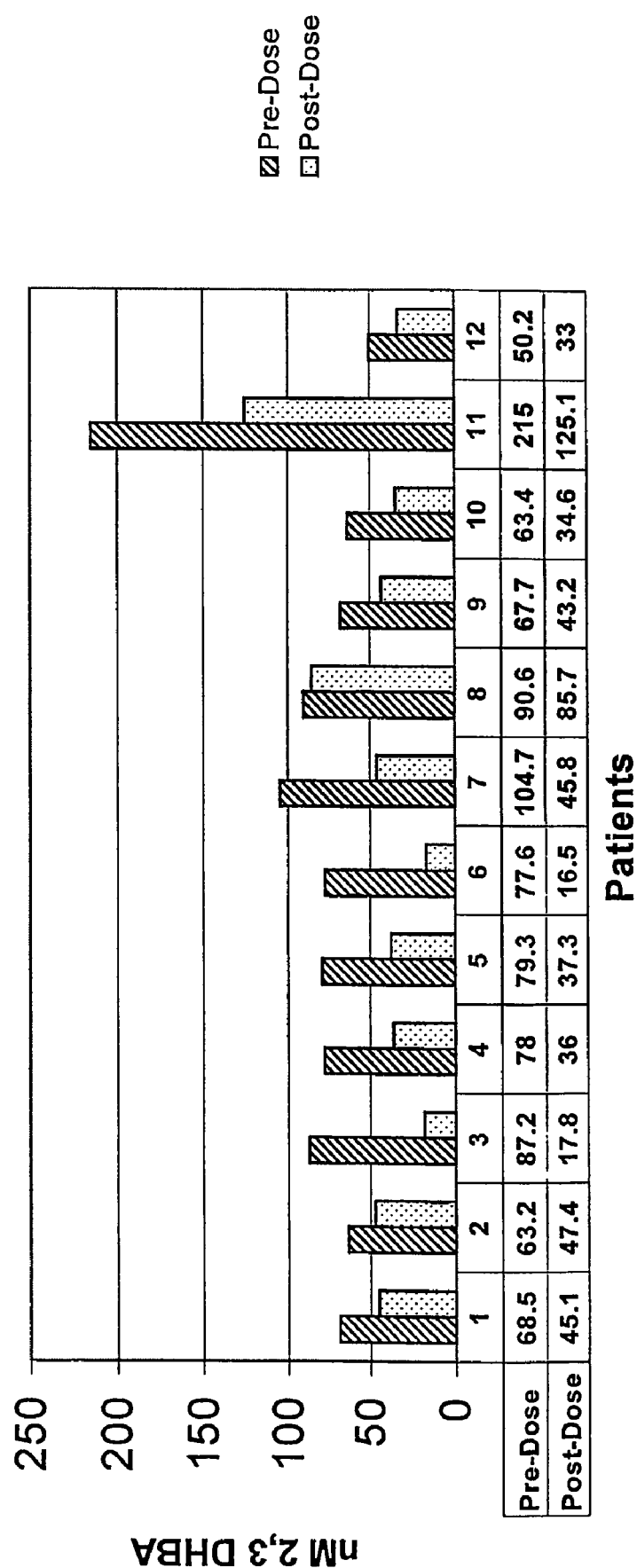
FIG. 6A indicates the DHBA concentrations in individual subjects both pre and post pramipexole treatment. Subjects 2, 3, 7 and 12 were non-ambulatory. Subjects 3 and 7 were ventilator dependent.
Figure 6B:
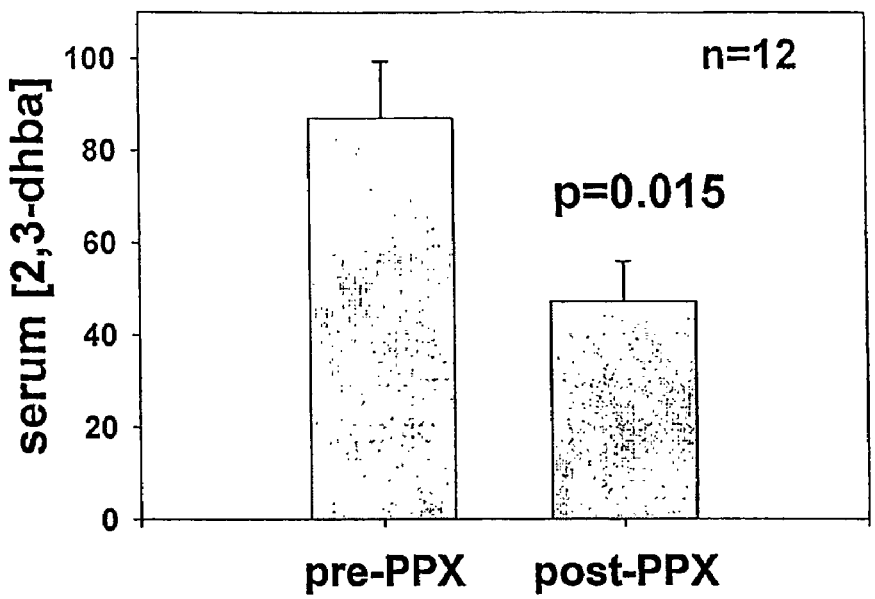
FIG. 6B provides the mean +/-SEM serum levels of 2,3-DHBA pre and post pramipexole treatment.
Figure 6C:
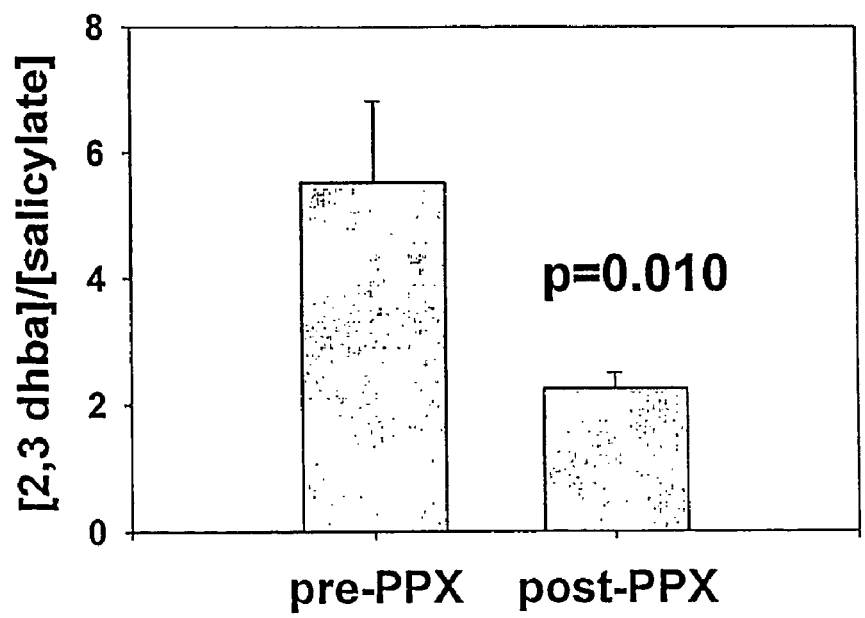
FIG. 6C provides the mean +/-SEM levels of serum of 2,3-DHBA concentration/salicylate pre and post pramipexole treatment.

Serum levels of 2,3-DHBA were compared pre- and post pramipexole treatment. Without exception, the individual serum levels of 2,3-DHBA were reduced (FIG. 6A). FIG. 6B shows the mean+/−SEM for serum 2,3-DHBA concentration in the ALS subjects before and after achieving stable pramipexole dosing. The mean reduction was about 45% and was significant at the p=0.015 level. Serum salicylate levels (µM) were unchanged both before (18.8+/−7.2, S.D.) and during (20.2+/−5.5, S.D.) pramipexole treatment. FIG. 6C shows that serum levels of 2,3-DHBA normalized to salicylate levels for each subject were reduced an average of 59% by pramipexole treatment; t-test showed this difference to be significant at the p=0.010 level.

Discussion

This study revealed that an approximate two-fold increase of in vivo oxidative stress was observed in ALS patients after oral aspirin loading, based on an increased production of 2,3-DHBA. The increase in 2,3-DHBA was observed at various stages of clinical disease progression, suggesting that this metabolite may serve as a reliable marker of increased oxidative stress throughout this disease process, but particularly in the early stages, when the diagnosis often remains uncertain. Because of the small population size, no attempt was made to correlate the level of 2,3-DHBA production with disease stage.

The present study also revealed that pramipexole therapy, at doses typically tolerated in Parkinson's disease, reduced in vivo oxidative stress in ALS subjects. Serum from 12 patients before and several weeks after reaching maximum tolerated doses of pramipexole revealed a reduction of about 45% of basal 2,3-DHBA and about 59% of basal 2,3-DHBA normalized to salicylate level. It is likely that pramipexole brought about this reduction in ROS production as a result of its free-radical scavenging/antioxidant properties. Pramipexole has been shown capable of reducing ROS production in both SY5Y neuroblastoma cells in vitro and rat striatum in vivo acutely exposed to complex I inhibition with methylpyridinium (Cassarino et al., J. Neurochem 1998; 71:295–301). Pramipexole also reduces brain ROS production in vivo following infusion of the neurotoxin 6-hydroxydopamine (Ferger et al., Brain Res 2000; 883:216–23), inhibits cytochrome C release and reduces brain lipid oxidation in vivo following treatment with the pro-neurotoxin MPTP [16].

Since approximately equivalent neuroprotective actions of pramipexole are observed in the R(+) and S(−) enantiomers, and since dopamine agonist actions reside primarily in the S(−) enantiomer, the ROS-scavenging actions likely have no relationship to dopamine agonist properties. If this is true, then the R(+) enantiomer of pramipexole should be tolerated in much higher doses than the S(−) enantiomer used in the present study, with the potential for increased antioxidative activity in vivo.

Oxidative stressors are well established in sporadic ALS, however the etiology of increased oxidative stress remains obscure. Markers of CNS oxidative stress damage in ALS include increased immunohistochemical staining in lumbar spinal cord for lipid peroxidation product, and increased spinal fluid levels of nitrotyrosine and nitrosylated manganese superoxide dismutase. These results are consistent with increased damage to ALS tissue by ROS that include nitric oxide derivatives.

Animal and cell models of ALS also provide insight into oxidative stress and motor neuronal vulnerability. ALS spinal cord motor neurons have reduced activity of cytochrome C oxidase, (studied histochemically) and such reduced electron transport chain function may serve to increase oxygen free radical production. Spinal cord microdialysis of mice carrying a mutant human SOD1 FALS gene revealed increased production of ROS and levels of malondialdehyde, consistent with that concept. Furthermore, it has been reported that a CuZn-SOD FALS mutation increased the vulnerability of spinal motor neurons to death from excitotoxicity, and the mechanism involved increased oxidative stress. Finally, increased oxidative stress in ALS may be responsible for increased markers of apoptotic cell death processes observed in ALS spinal cord, and for involvement of caspases in motor neuron death in a FALS mouse model.

Mitochondrial pathology occurs early in the course of experimental motor neuron disease. These structures are not only sensitive to oxidative injury, but their dysfunction leads to accelerated free radical production and possible damage to mitochondrial DNA. Visualization of mitochondrial function in ALS muscle biopsies revealed reduced activity of complex I, and ultrastructural analysis of ALS anterior horn cell dendrites revealed aggregated, dark mitochondria. Selective loss of glial excitatory amino acid transporter-2 (EAAT2) around degenerating anterior horn cells in ALS may reflect additional protein damage that could contribute to increased excitotoxicity.

Oxidative damage in ALS may therefore represent a primary neurodegenerative process, a secondary epiphenomena of motor neuron mitochondrial pathology, or a combination of both. Cybrid studies with amplification of SALS mitochondrial genes have shown that increased oxidative stress in SALS can be understood in terms of a primary mitochondrial genetic etiology. How mitochondrial DNA becomes defective in SALS is not known; both maternally inherited and sporadically acquired mechanisms are possible.

The use of salicylate loading and 2,3-DHBA measurements as an estimate of relative in vivo oxidative stress levels has been applied to adult-onset diabetes, liver dysfunction in alcoholics and arthritis. Multiple oxidizing species can contribute to the production of 2,3-DHBA, including hydroxyl radical and peroxynitrite anion. Thus, a particular ROS source cannot be assigned for the observed 2,3-DHBA levels, nor can the tissue source(s) of increased salicylate hydroxylation be defined.

In summary, basal serum levels of 2,3-DHBA, a marker of oxidative stress, were found to be increased in a cohort of SALS subjects, and these levels were reduced following treatment with pramipexole. As is shown in FIG. 6 individual serum levels of 2,3 DHBA decreased in ALS patients after treatment with S(−) 2-amino-4,5,6,7-tetrahydro-6-propylaminobenzathiazole. In particular, the patients were administered orally a daily dose of 3–6 mg of S(−) 2-amino-4,5,6,7-tetrahydro-6-propylaminobenzathiazole for seven weeks. At the end of seven weeks serum samples were taken and the concentration of 2,3 DHBA was measured and compared to 2,3 DHBA levels in serum samples taken prior to treatment. These data demonstrate that treatment with pramipexole lowers oxidative stress in vivo in ALS patients.

EXAMPLE 3

Effectiveness of Pramipexole in Reducing Mptp Induced Oxidative Stress in vivo

Methods

Male C57BL/6 mice received daily R(+) pramipexole dihydrochloride in drinking water for 8 weeks at doses calculated to provide 0, 10, 30 or 100 mg/kg/day. On the day of the study the mice were injected with 30 mg/kg s.c. of the neurotoxin N-methyl-4-phenyl-1,2,3,6-tetrahydropyridine (MPTP) to increase oxidative stress in the brain. One hour later the mice were injected with 100 mg/kg i.p. of sodium salicylate. One hour after salicylate injection the mice were killed and forebrains analyzed for 2,3-dihydroxybenzoic acid (2,3-DHBA) content.

As shown in FIG. 7 the results show that 30 and 100 mg/kg/day treatment with R(+) pramipexole significantly reduced forebrain oxidative stress produced by MPTP. Toxicology studies have also been conducted and no evidence of adverse effects were detected. In particular, an 8 week toxicology study was performed in the mice given R(+) PPX in their drinking water. All their major organs were examined pathologically and no lesions were found.

What is claimed is:

1. A method of treating ALS in a patient in need thereof, comprising administering to the patient a pharmaceutical composition comprising a pharmaceutically acceptable carrier and an effective amount of pramipexole, wherein greater than 90% of the pramipexole is R(+) 2-amino-4,5,6,7-tetrahydro-6-propylaminobenzathiazole.

2. The method of claim 1 wherein greater than 95% of the pramipexole is R(+) 2-amino-4,5,6,7-tetrahydro-6-propylaminobenzathiazole.

3. The method of claim 1 wherein greater than 99% of the pramipexole is R(+) 2-amino-4,5,6,7-tetrahydro-6-propylaminobenzathiazole.

4. The method of claim 1 wherein the pramipexole is administered in an amount effective as a neuroprotectant.

5. The method of claim 1 wherein about 3 mg to about 500 mg of pramipexole is administered daily.

6. The method of claim 1 wherein the pramipexole is R(+) 2-amino-4,5,6,7-tetrahydro-6-propylaminobenzathiazole.

7. The method of claim 1 wherein between about 3 mg to about 6 mg is administered daily.

8. The method of claim 1 wherein about 30 mg/kg to about 100 mg/kg of pramipexole is administered per day.

9. The method of claim 1 wherein the pramipexole is administered via a route selected from the group consisting of transdermal, topical, oral, intravenous, intramuscular, intra-arterial, intramedullary, intrathecal, intraventricular, subcutaneus, intraperitoneal, intranasal, enteral, sublingual, and rectal.

10. The method of claim 1 wherein said the pramipexole is administered in a dosage escalation regime.

\* \* \* \* \*

UNITED STATES PATENT AND TRADEMARK OFFICE
CERTIFICATE OF CORRECTION

PATENT NO.        : 7,157,480 B2
APPLICATION NO.   : 10/496714
DATED             : January 2, 2007
INVENTOR(S)       : James P. Bennett, Jr.

It is certified that error appears in the above-identified patent and that said Letters Patent is hereby corrected as shown below:

Claim 9, column 18, line 39, replace "subcutaneus" with --subcutaneous--.
Claim 10, column 18, line 41, delete "said".

Signed and Sealed this

Twenty-first Day of August, 2007

JON W. DUDAS
*Director of the United States Patent and Trademark Office*